United States Patent [19]

Summers et al.

[11] Patent Number: 5,037,431
[45] Date of Patent: Aug. 6, 1991

[54] SURGICAL LIQUID LANCE APPARATUS

[75] Inventors: David A. Summers; William V. Stoecker; James Blaine, all of Rolla

[73] Assignee: The Curators of The University of Missouri, Columbia, Mo.

[21] Appl. No.: 431,374

[22] Filed: Nov. 3, 1989

[51] Int. Cl.⁵ ............................................. A61B 17/32
[52] U.S. Cl. .................................. 606/131; 606/167; 604/22
[58] Field of Search ..................... 604/22, 43, 35, 131, 604/150, 151; 606/131, 159, 167

[56] References Cited

U.S. PATENT DOCUMENTS

| | | |
|---|---|---|
| 4,445,517 | 5/1984 | Field . |
| 4,465,470 | 8/1984 | Kelman . |
| 4,516,398 | 5/1985 | Wuchinich . |
| 4,531,934 | 7/1985 | Kossovsky et al. . |
| 4,560,373 | 12/1985 | Sugino et al. ......................... 604/30 |
| 4,578,058 | 3/1986 | Grandon . |
| 4,637,814 | 1/1987 | Leiboff . |
| 4,913,698 | 4/1990 | Ito et al. ............................... 604/22 |

FOREIGN PATENT DOCUMENTS

| | | | |
|---|---|---|---|
| 232678 | 8/1987 | European Pat. Off. ............ | 606/159 |
| 258901 | 9/1988 | European Pat. Off. ............ | 606/167 |
| 3421390 | 12/1985 | Fed. Rep. of Germany ...... | 606/159 |
| 234608 | 4/1986 | U.S.S.R. ............................... | 606/167 |

OTHER PUBLICATIONS

"Surgical Cutting of the Liver by Water Jet", 9th Inter-nat'l Symposium on Jet Cutting Technology, Sendar, Japan Oct., H-6, 1988, pp. 629–639.

"A Critical Examination of the Use of Water Jets for Medical Applications"; M. Vegay, 5th Am. Water Jet Conf.; 8/29-31/89; Toronto, Can.; pp. 425–448.

Primary Examiner—Stephen C. Pellegrino
Assistant Examiner—Ralph A, Lewis
Attorney, Agent, or Firm—Litman, McMahon & Brown

[57] ABSTRACT

A hand-held surgical apparatus with supporting equipment comprising a mechanism for producing a pressurized jet of fluid which is sufficiently energetic to fragment diseased human and animal tissue without damaging adjacent healthy tissue. Preferably the apparatus includes a jet of fluid which impinges obliquely onto the operative area such that diseased tissue underneath overlying healthy tissue may be fragmented, especially finger-like extensions from tumorous growths of the skin. The jet rotated about a generally vertical axis such that the points of impact of the water from the jet upon the operative area describes circular patterns, thereby effectively and quickly distributing fragmenting energy over a wide operative area. A supporting vacuuming apparatus for aspirating effluent or expended fluid and fragmented tissue from the operative site. A surgical procedure for removing tumorous growths at the cutaneous surface includes the steps of impinging a growth on the skin with a jet of pressurized fluid using the apparatus.

20 Claims, 2 Drawing Sheets

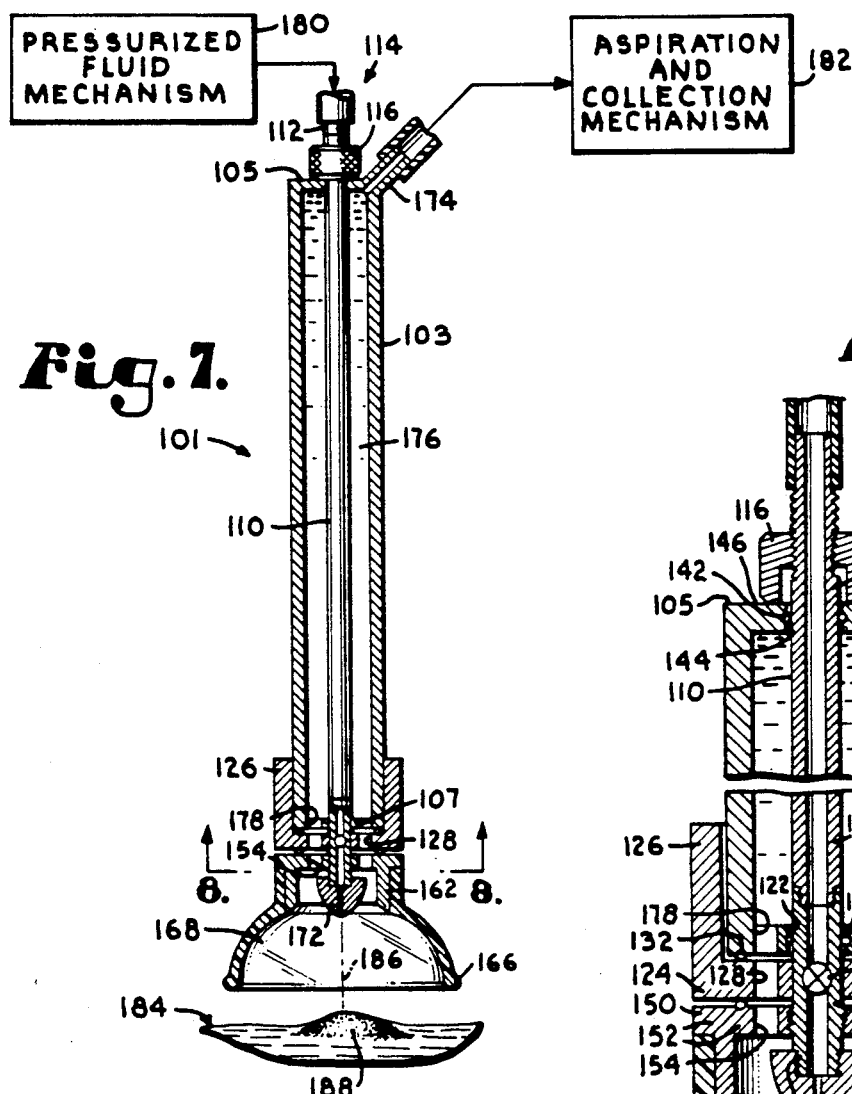

SURGICAL LIQUID LANCE APPARATUS

FIELD OF THE INVENTION

The present invention relates to an apparatus and method for removing growths from skin or other living tissue utilizing high pressure water jets that remove the unwanted growths without substantially damaging healthy tissue.

BACKGROUND OF THE INVENTION

Skin cancer and related growths both on the skin and on other living tissue are relatively common maladies apparently occurring with increasing frequency partially due to depletion of ozone in the upper atmosphere. Such growths are sometimes characterized by finger-like extensions or striations therefrom. Early detection and removal of these growths in their entirety can avoid the much more complicated and sometimes fatal consequences of delayed or insufficient treatment. It is especially important to remove cancerous growths before such growths metastasize to other parts of the body.

Surgical excision is the first method usually considered for removal of skin neoplasms as such an approach has historically proven most advantageous for removal of small tumors. Surgical excision has the disadvantage of allowing a significant number of recurrences because of the clinically hard to see or invisible finger-like extensions of tumorous growth which may extend beneath otherwise healthy appearing skin beyond the area being treated during the excision. Further, tumors which occur in areas where it would be difficult to obtain closure are not generally considered for simple excision.

A second technique previously used, known as Mohs' Technique, involves performing layered excisions which are fixed and carefully examining each layer for any cancerous growth to ensure no cancerous tissue remains. A variation of this is the fresh tissue variation of the Mohs' technique in which sequential horizontal sections are removed from the surface one at a time and microscopically studied until no cancerous material is found. In this manner the tumor is traced to its farthest and deepest extent which does allow for removal of all of the finger-like extensions which might otherwise escape detection using conventional surgical techniques. Unfortunately, substantial amounts of healthy tissue are unavoidably simultaneously surgically removed using this technique. Also, the use of the Mohs' technique can be costly and very labor intensive as each section must be prepared and tested before the next section is taken while the patient waits.

A third technique is electrodessication and curettage (ED & C). The skin is curetted with a large and a small curette in an attempt to uncover all extensions of the tumor. The affected skin is then superficially dried and charred using a monopolar probe having a source of moderately high voltage, low amperage alternating current. The drying and charring cycle is then repeated two more times, with the resulting wound left to heal by secondary intention. The electrodessication and curettage technique has two major problems: one being the relatively high rate of recurrence, and the other being the cosmetic defect normally remaining after the wound has healed.

Cryosurgery is another relatively simple technique for ablation of epitheliomas. Often, the physician curettes the tumor prior to the cryotherapy. Generally the affected tissue is frozen to $-60°$ C. in an ice ball. After two freeze-thaw cycles, the wound is allowed to heal. Cryosurgery may generally leave hypertrophic scars and can cause excessive tissue destruction and scar formation with concurrent deformity of adjacent otherwise healthy tissue. Other problems encountered with cryosurgery include pain, significant cutaneous necrosis, risk of infection, and local neuropathy.

Radiation therapy has also been used to treat such cancerous growths. Radiation therapy has two primary drawbacks. The first is the secondary injury that often follows the use of radiation; the second is the extremely high investment cost of the equipment needed for radiation therapy.

The use of a pressurized narrow jet of fluid as a means of removing softer tissue without damage to adjacent healthy tissue provides the ability to remove only the diseased tissue leaving the healthy tissue viable and the resulting wound relatively easy for the body to repair with relatively little disfigurement or secondary damage to surrounding tissue. The pressure source for the jet is adjusted such that the energy released at impact of the liquid of the jet with the affected tissue is sufficient to allow the jet to penetrate not only the main tumor mass, but also into the long, yet narrow and initially clinically invisible, tendrils of growth which radiate outward from the main tumor, thereby allowing the removal of the diseased tissue without damage to the adjacent healthy tissue.

SUMMARY OF THE INVENTION

A surgical liquid lance in accordance with the present invention includes an apparatus for producing a fluid jet to remove diseased or tumor-like tissue from a living organism, especially from human skin, without substantial damage to healthy tissue in the immediate proximity of diseased tissue to be treated.

One embodiment of the apparatus includes a spinable nozzle. Water, as a preferred fluid, is supplied to the nozzle under pressure. Energy stored in the pressurized water is then used for two purposes: (1) to hydrodynamically spin a nozzle, and (2) to form narrow, relatively well-defined, kinetically energetic fluid jet or jets of fluid which emerge from the nozzle and which are directed at tumorous or diseased tissue to be removed by the surgeon operating the apparatus. Diseased tissue is not as resilient as healthy tissue. As a result, the diseased tissue is much more easily removed than the healthy tissue, thereby providing the ability to selectively remove diseased tissue while leaving healthy tissue intact. The pressure of the water is preferably adjustable such that the energy released by impact of the fluid jet on the tissue in association with an appropriate residence time for the particular tissue to be removed is sufficient to fragment the tumorous or diseased tissue but is insufficient to damage the surrounding healthy tissue.

The spinning of the nozzle effectively directs the fluid jet to encompass the entire operative area such that the entire diseased or tumorous area is exposed to the tissue fragmentation process, although the surgeon can selectively guide the fluid jet over portions of the tumor that are larger or need additional residence time to remove. Preferably, the nozzle is angled such that the fluid jet impinges on the tissue at an angle with respect to the perpendicular so that the fluid jet tends to impact on and migrate into finger-like extensions of the diseased tissue that lies beneath otherwise healthy tissue thereby selectively fragmenting and removing the diseased tissue in the fingers. In particular, the jet impacts obliquely on the operative site such that the fragmentation process more effectively penetrates and removes the finger-like extensions of the diseased tissue that extend under an overlapping lip of healthy skin tissue.

The high pressure fluid jet is directed at the operative area until all of the diseased or tumorous tissue has been fragmented and removed from the operative site.

The apparatus includes a vacuum system to provide a reduced ambient pressure in the region immediately adjacent to the operative site such that the fragmented tissue and the expended fluid or effluent from the jets can be aspirated from the operative site and collected for disposal or, where desired, for further diagnosis.

In accordance with the present invention, a method is provided to remove tumors or related diseased tissue using the above described apparatus. An important feature of the method, and one which represents a distinct advantage over other conventional treatments now in use, is that this method will effectively remove all diseased tissue without the large scale excision or destruction of adjacent healthy tissue which is inherent with other conventional treatments.

It is further noted that this method can be carried out relatively rapidly with minimal pain and discomfort to the patient. Since large scale removal of tissue is not anticipated with application of the present method, for most applications it will be possible to minimize cosmetic problems and to quickly promote regrowth of healthy tissue in the region where diseased tissue has been removed.

OBJECTS OF THE INVENTION

Therefore, the objects of the present invention are: to provide an apparatus to produce a pressurized jet of fluid for surgical purposes; to provide such an apparatus having a control mechanism to allow selective adjustment of the pressure of the fluid jet such that the impact energy of the fluid jet with the operative tissue is sufficient to remove lesser resilient diseased tissue without harming adjacent, more resilient healthy tissue; to provide such an apparatus having a nozzle positioned and constructed such that the fluid jet impinges tissue at an oblique angle; to provide such an apparatus wherein the nozzle is rapidly rotated by the fluid pressure so as to cause the point of impact of the fluid jet to describe a generally circular pattern; to provide such an apparatus that allows selective penetration and fragmentation of diseased tissue in finger-like extensions from tumorous growths without harming surrounding or overlying healthy tissue; to provide such an apparatus that allows fluid jets to reach under overlying healthy skin tissue to remove underlying diseased tissue while leaving the healthy tissue intact; to provide such an apparatus and a method for using the apparatus that minimize or eliminate pain, trauma and post-operative bleeding; to provide such an apparatus with a vacuuming system such that the fragmented diseased tissue can be aspirated for disposal or further analysis and diagnosis; to provide such a vacuuming system wherein the expended fluid is aspirated away from the operative area; and to generally provide such a surgical apparatus that is relatively easy to operate, simple to clean and maintain, avoids unnecessary removal of healthy tissue, minimizes litigeous exposure, and otherwise efficiently and effectively performs the functions of its intended purpose.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 6 is an enlarged and fragmentary view of the apparatus, taken along line 6—6 of FIG. 2.

FIG. 7 is a cross-sectional and partially schematic view of a modified liquid lance apparatus in accordance with the present invention.

FIG. 8 is an enlarged bottom plan view of the modified apparatus, taken along line 8—8 of FIG. 7.

FIG. 9 is a cross-sectional and fragmentary view of the modified liquid lance apparatus of the preset invention.

DETAILED DESCRIPTION OF THE INVENTION

Figure 1:
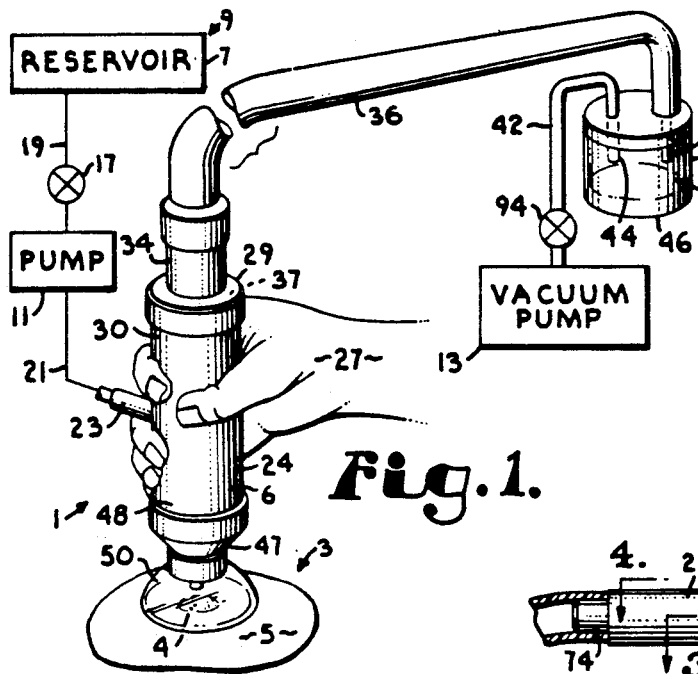
FIG. 1 is a partially schematic and fragmentary perspective illustration of a liquid lance apparatus in accordance with the present invention shown held by a surgeon over a region of skin of a patent having a tumor to be removed by the apparatus.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

The reference numeral 1 generally designates a liquid lance apparatus in accordance with the present invention. The reference numeral 3 generally designates cutaneous flesh or skin of a patient including a diseased or tumorous area 4 and surrounding healthy tissue 5 in close proximity thereto. The apparatus 1 includes a hand-held portion 6 along with equipment external thereto including fluid supply means comprising a fluid reservoir 7 containing a fluid 9, a sterilizable fluid pump 11 flow connected to the hand-held portion 6 and vacuum system means comprising a vacuum pump 13 and a collector 15 also flow connected to the hand-held portion 6. The collector 15 can be a beaker, cannister or other suitable container.

The fluid 9 may be water, sterile saline solution or the like that is appropriate for contact with the flesh or other tissue exposed thereto during the course of utilizing the present invention. The flow of the fluid 9 from the reservoir 7 is controlled by a valve 17. When the valve 17 is placed in its "open" configuration, a length of hose or tubing 19 directs the fluid 9 from the reservoir 7 to the pump 11. The pump 11 preferably has a variable output pressure and, when operating, develops sufficient hydrodynamic pressure in the fluid 9 to force the fluid 9 through the remainder of the hand-held portion 6, as is more clearly described hereinafter.

After passing through the pump 11, the fluid 9 is directed through a length of flexible tubing 21 which is removably and frictionally secured to a hollow fluid input nipple 23. The nipple 23 is constructed of stainless steel or other suitable material.

The fluid input nipple 23 is threadedly secured to a lance body 24 in a partially tapped bore 25. The body 24 is constructed of steel or other suitable material. External flats on the surface of the nipple 23 assist with the securement thereof to the body 24. The bore 25 flow connects the interior of the nipple with an inner circumferential surface 26 of the body 24.

The body 24 is preferably cylindrical in shape and is dimensioned and designed to be conveniently and firmly graspable by a surgeon's hand 27 during an operative procedure. In practice, the body 24 has a diameter in the range of approximately one to three inches. The body 24 and attachments thereto are intentionally designed in such a manner that the apparatus can be indiscriminately used by either a right-handed or left-handed surgeon.

An upper end cap 29 telescopes over an upper end 30 of the body 24 and is frictionally, threadedly, or otherwise secured thereto. The upper end cap 29 has a generally annular extension 34 extending upwardly therefrom. The extension 34 has a throughbore 35 such that a flexible hose or tubing 36 is removably secured to the extension 34 so as to flow communicate with an upper cavity 37 enclosed within the body 24 and covered by the upper end cap 29. Alternatively the extension 34 can be reduced in diameter such that a smaller diameter hose 36 can be attached thereto so long as a chamber 38 within the end cap 29 is sufficiently dimensioned to permit uninhibited vertical movement of a spindle hub 39 therein. The tubing 36 is frictionally secured, by clamp, retaining ring, or other suitable device, to the upper end cap extension 34. The upper end cap 29 is dimensioned such that the cavity 37 and chamber 38, surround and enclose the upper end of the spindle hub 39 allowing the hub 39 to freely turn therein while providing sufficient passage for aspirated fluid and fragmented tissue to freely pass therethrough as hereinafter described.

An opposite end of the tubing 36 is secured to an input port 40 of the collector 15, and another length of tubing 42 interconnects an output port 44 of the collector 15 with the vacuum pump 13. The collector 15 has an open gap 45 between the input port 40 and the output port 44 thereof such that aspirated liquids and solids 46 fall out of the gaseous and vapor stream passing through the collector 15 and are preserved and collected therein for disposal or subsequent analysis and diagnosis.

A lower end cap 47 telescopes over a lower end 48 of the body 24. End caps 29 and 47 are constructed of aluminum or other suitable material. A shield 49 constructed of clear plastic such as poly(methyl methacrylate)-type polymers marketed under the trademark Plexiglas or other transparent material is threadedly, adhesively, or otherwise secured to the distal end 50 of the lower end cap 47. The transparent portion of the shield 49 is comprised of a material which can be treated to minimize adherence of fragmented tissue and fluid droplets to the inner surface thereof which would otherwise interfere with and obstruct the surgeon's view during use. The shield 49 may be bell-shaped, cylindrical, spherical, or the like and helps to provide a viral barrier by preventing fluid 9 contaminated with tissue, that may contain microorganisms such as viruses, from ricocheting away from the operative site. The shield 49 is further designed such that the surgeon can clearly and unobstructedly view the operative area by looking obliquely through the shield 49 at the operative tissue area 3. A cavity 51 contained within the lower end cap 47 and a cavity 52 contained within the shield 49 in conjunction with the tissue area 3 substantially encloses the lower portion of the hand-held portion 6 except for a slight in flowing airflow when the shield 49 is positioned in close proximity to the tissue area 3 being treated.

Figure 5:
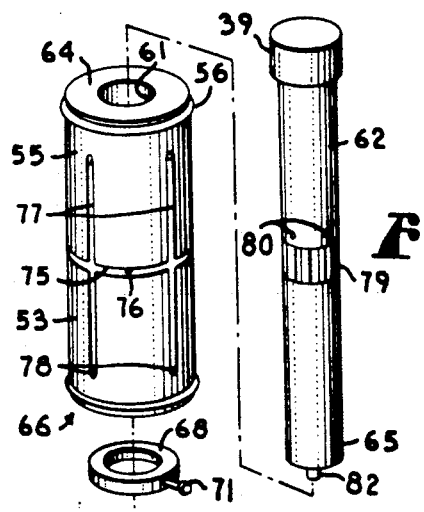
FIG. 5 is an enlarged and exploded view of a spindle, a housing, and an annular retaining ring of the apparatus.

The body 24 is axially throughbored to form the bore 26 to slidably receive a cylindrically shaped housing 53, see FIG. 5. The housing 53 is constructed of stainless steel or other suitable material. A groove 54 is machined, molded or otherwise formed into a circumferential surface 55 thereof near each end of the housing 53 to receive an O-ring type, flexible washer 56. The outer diameter of the housing 53 and the grooves 54 are dimensioned such that the O-ring washers 56 are compressed between the housing 53 and the interior of the annular body 24, forming liquid seals therebetween, the housing 53 and body 24 being generally coaxial relative to each other.

Figure 3:
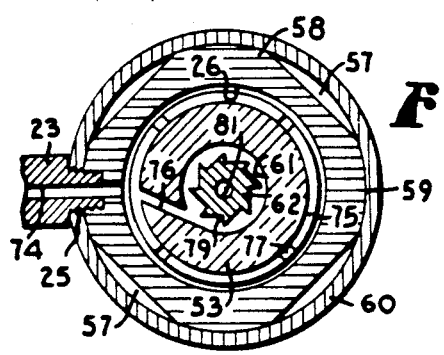
FIG. 3 is an enlarged cross-sectional view of the apparatus, taken along line 3—3 of FIG. 2.
Figure 4:
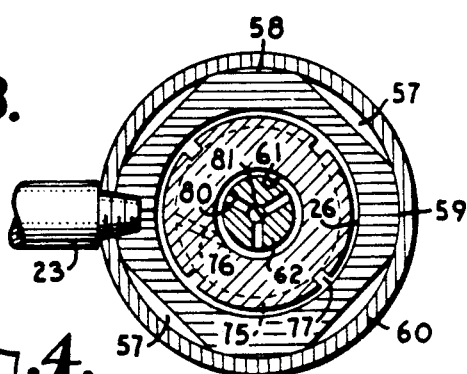
FIG. 4 is an enlarged cross-sectional view of the apparatus taken along line 4—4 of FIG. 2.

Besides forming a liquid seal, the O-ring washers 56 serve to frictionally secure against the displacement of the housing 53 relative to the body 24 along the common axes thereof. The longitudinal dimension of the housing 53 is less than the longitudinal dimension of the bore 26 through the body 24 such that the displacement of the housing 53 relative to the body 24 can be readily adjusted by manual manipulation while the washers 56 remain disposed within the bore 26. Vacuum channels 57, as shown in FIGS. 3 and 4, form fluid flow passageways through the body 24 such that the lower cavities 51 and 52 communicate with the upper cavity 37. In the illustrated embodiment, the body 24 is constructed from a rectangular block 58 with rounded outer corners 59 circumscribed by an outer cylindrical sleeve 60, as shown in cross-section in FIG. 3, thereby forming four chord-like channels 57 communicating between the cavities 37 and 51.

Figure 2:
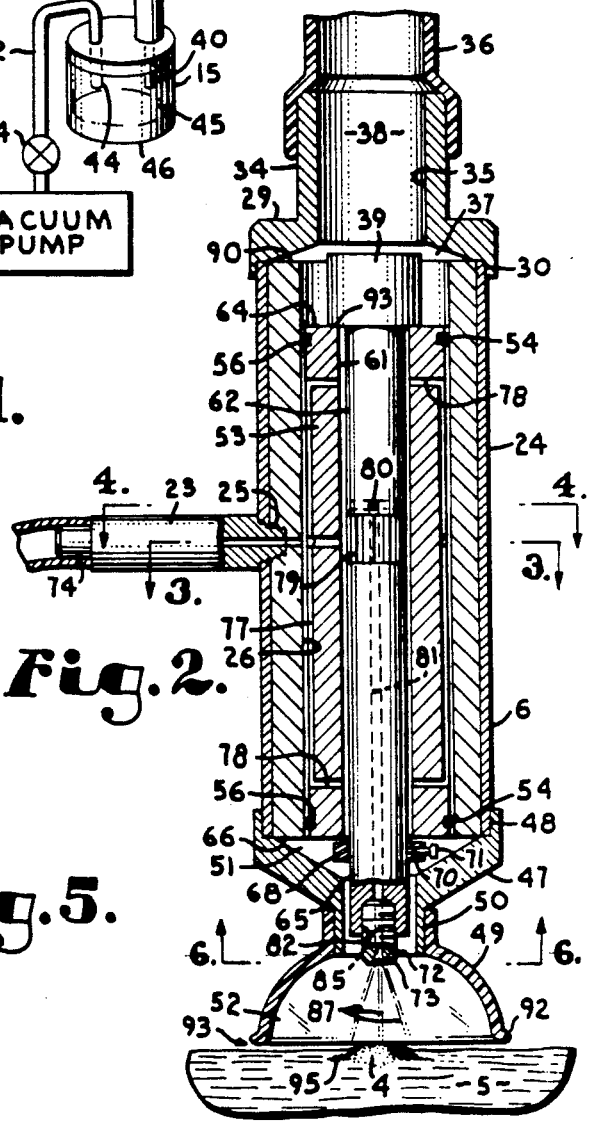
FIG. 2 is a fragmentary and enlarged cross-sectional view of the apparatus positioned over a portion of the skin of the patient and the tumor.

The housing 53 is through-bored along and concentric with its vertical axis, as shown in FIGS. 2 and 3 so as to form a central bore 61. A cylindrically-shaped spindle 62, has a diameter slightly less than the diameter of the bore 61, such that the spindle 62 is slidably insertible therethrough. The spindle 62 is constructed of brass or other suitable material. The tolerance between the spindle 62 and the bore 61 is designed such that the spindle 62 can freely rotate axially therein without excessive lateral movement.

The hub 39 is attached to, or an integral part of, the upper end of the spindle 62 and has a diameter greater than the diameter of the throughbore 61 of the housing 53. The hub 39 rests against and is supported by an upper planar face 64 of the housing 53 such that a lower portion 65 of the spindle 62 extends beyond and protrudes below a lower planar face 66 of the housing 53. The diameter of the hub 39 is dimensioned smaller than the diameter of the bore 26 of the body 24 such that adjustment of the relative displacement between the housing 53 and the body 24 will not cause the body 24 to interfere with the rotation of the spindle 62.

An annular retainer ring 68 has an inner diameter dimensioned slightly larger than the diameter of the spindle 62 such that the lower end 65 of the spindle 62 is slidably insertible therethrough and the ring 68 has an outer diameter dimensioned greater than the diameter of the throughbore 61 of the housing 53. The ring 68 has a transverse threaded bore 70 that communicates between an outer circumferential surface of the ring 68 with an inner circumferential surface thereof. A set screw or bolt 71 of sufficient length to completely traverse the threaded bore 70 of the annular ring 68 is threadedly inserted through the bore 70 such that the annular ring 68 can be slidably telescoped over the lower end 65 of the spindle 62 and frictionally secured to the spindle 62 by threadedly advancing the set screw 71 against the spindle 62 as shown in FIG. 2. The outer diameter of the ring 68 and the transverse extension of the screw 71 must be such that the ring 68 and screw 71 can freely rotate within bore 26 without interference therewith. Alternatively, it is foreseen that the inner surface of the annular ring may be threaded to mate with tapped threads on the lower end of the circumferential surface of the spindle such that the need for the set screw can be eliminated.

The manner in which the spindle 62 is slidably inserted through the housing 53 and the annular ring 68 is secured to the projecting lower end 65 of the spindle 62 is such that an assembly including the spindle 62, the housing 53, and the annular ring 68 is readily and easily disassembled by unseating the set screw 71, removing the annular ring 68 from the spindle 62, and extracting the spindle 62 from the housing 53, thereby exposing the inner surfaces of these parts for cleaning and sterilization.

The lower end cap 47 is generally conically-shaped, tapering inwardly toward the distal end thereof as shown in FIG. 2. The lower end cap 47 is dimensioned such that the lower end 65 of the spindle 62, the annular ring 68, and a nozzle 72 are contained well within the lower cavity 52 while maintaining the integrity thereof for vacuuming purposes and for maximum viewing convenience through the shield 49 by the surgeon. The axial height of the shield 49 is such that sufficient surface tissue area 3 is readily visible to the surgeon, while maintaining each orifice 73 of the nozzle 72 in relatively close proximity to the surface of the operative tissue area 3.

A passageway 74 which passes longitudinally through the fluid input nipple 23 provides a channel for flow of the fluid 9 from the tubing 21 through the body 24 to the throughbore 26 and also flow communicates with a circumferential groove 75 around the outer circumferential surface 55 of the housing 53. Along a plane perpendicular to the longitudinal axis of the housing 53, a semi tangential bore 76 flow communicates between the circumferential groove 75 and the bore 61.

Flow communicating with the groove 75 are four longitudinal grooves 77 along the circumferential surface of the housing 53. Alternatively, the number of grooves 77 may be increased or decreased as required for any particular application of the present invention. Each groove 77 stops short of the circumferential grooves 54 provided for the O-ring washers 56. At each end of each groove 77, a radial bore 78 flow communicates between the grooves 77 and the bore 61.

The spindle 62 is configured with symmetrically and angularly spaced impeller or turbine vanes 79 which are cut, machined or otherwise formed into the circumferential surface thereof. The vanes 79 of the spindle 62 are aligned such that the fluid 9 emerging from the bore 76 impinges directly onto the vanes 79. The impulse transmitted to the vanes 79 of the spindle 62 by the flow of the fluid 9 emerging from the bore 76 causes the spindle 62 to rotate about its axis within the housing 53. The orientation of the vanes 79 can be such that the spindle 62 can be caused to rotate either clockwise or counterclockwise as viewed vertically downward. The bore 76 is accordingly angled such that the fluid 9 emerging from the bore 76 more directly impacts with the vanes 79, thereby imparting greater kinetic energy directly thereto.

In close proximity to the vanes 79 in the spindle 62 are three radial bores 80 forming passageways from the immediate vicinity of the vanes 79 to the longitudinal axis of the spindle 62. Alternatively, it is foreseen that radial bores may be positioned within the cylindrical region of the vanes instead of being positioned to one side of the vanes, as shown in FIG. 2.

A partial axial bore or jet channel 81 flow communicates between the intersection of the bores 80 and the distal end of the spindle 62. At the lower end of the spindle 61 and coaxial therewith is a threaded bore 82, as shown in FIG. 2, to threadedly receive the nozzle 72. Alternatively, it is foreseen that the lower end may be tapped to mate with a partially tapped bore in the nozzle or a nipple may be interposed between the lower end of the spindle and the nozzle. The nozzle 72 is designed to be readily removable to allow exchanging nozzles having different characteristics as required for any particular application of the current invention.

The nozzle 72 includes a bore 85 such that jets 87 of fluid emerge from the orifices 73 of the nozzle 72. The jets 87 have small, consistent, and well defined cross-sectional areas so that kinetic energy is focused on and directed by each jet 87 to a small region of the operative tissue 3. The cross-section of the jets 87 whereat each impinges on tissue area 3 may be varied from relatively small or needle-like to wider for various applications. It is foreseen that a single jet may emerge from a nozzle. The orifice bores 73 are angularly oriented such that the trajectories of the jets 87 emerging from the nozzle 72 radiate outward and downward from the nozzle 72 at an angle of approximately 15° from the longitudinal axis of the spindle 62 and nozzle 72. In particular, the interchangability feature of the nozzle 72 facilitates the use of various nozzles having (1) larger or smaller orifices, for example, in the range from 0.001 to 0.030 inches; (2) more orifices, for example, four orifices pointed different directions and each angled with respect to the axis of rotation; (3) orifice outlets radially spaced greater than or less than 15° from the axis of rotation thereof, or other variations and characteristics depending on the particular application to which the present invention is being applied.

In the present embodiment, the nozzle 72 has a single bore 73, with an inside diameter of approximately 0.007 inches. Three important factors must be considered in the diameter of the jets for any particular application. First, the diameter must be sufficiently small such that the impact energy of the jets 87 with the operative tissue 3 effectively permeates the finger-like projections from the tumorous growths 4. Second, the diameter must be sufficiently small such that any inertial impulse forces, which must be resisted by the surgeon, are minimal. Third, the volume of expended fluid, which must be aspirated away from the operative site, is preferably kept to a minimum.

The axial length of the hub 39 is preferably sufficient for the hub 39 to project above an uppermost extremity 90 of the body 24, even when the housing 53 and spindle 62 are adjusted to the lowermost position relative to the body 24.

The diameter of the throughbore 35 of the extension 34 is dimensioned larger than the diameter of the hub 39 such that the extension 34 will not interfere with the hub 39 even when the housing 53 and spindle 62 are adjusted to the uppermost position relative to the body 24. In addition, the tolerance between the circumferential surface of the hub 39 and the extension bore 35 is such that the aspirated fluid containing fragmented tissue can freely pass from the channels 57 through the cavities 37 and 38 to the tubing 36 enroute to the collector 15.

During actual operation of the apparatus of the present invention, the tubes 19 and 21 are connected to communicate the fluid 9 in the reservoir 7 with the pump 11 and the lance 1, and the tubes 36 and 42 are connected to communicate the cavities 37, 38, 51 and 52 with the collector 15 and the vacuum pump 13. The surgeon then settles the hand-held portion 6 of the apparatus 1 directly over the diseased or tumorous region of tissue 4 to be removed such that an outer end 92 of the shield 49 is placed in close proximity to the operative tissue area 3. The hand-held portion 6 is positioned such that the orientation of the longitudinal axis of the spindle 62 is approximately perpendicular to the outer surface of the operative area of tissue 3.

The vacuum pump 13 which aspirates the expended fluid and the pump 11 which pressurizes the fluid are then placed in operation. The pump 11 pressurizes the fluid 9 to a pressure preferably in the range of 100 to 250 pounds per square inch (although other pressures are usable for certain purposes), forcing the fluid 9 through the apparatus 1 and causing the spindle 62 to rotate. The exact rotational velocity of the spindle 62 is not critical. In practice, however, the rotational velocity is of the order of several hundred revolutions per minute. If necessary, the rate of rotation can be controlled by adjusting the pressure imparted to the stream of fluid just prior to its emission from the bore 76 by controlling either the valve 17 or the action of the pump 11, as long as the impact energy of the jets 87 is maintained in a range whereby the diseased tissue 4 is fragmented while the healthy tissue 5 remains intact. Some of the fluid 9 entering the groove 75 is forced along the grooves 77 and through the bores 78, forming a circumferential liquid bearing along the bore 61 between the housing 53 and the spindle 62. It is foreseen that thin, low friction rings (such as are sold under the trademark Teflon) may be slidably inserted into the housing bore 61 and telescoped over the ends of the spindle 62 to provide a bearing surface between the housing 53 and the spindle 62.

Some of the fluid 9 forming the liquid bearing between the housing 53 and the spindle 62 leaks from the upper end of the bore 61 between the spindle 62 and the housing 53 and between the hub 39 and the upper housing face 64 such that any fragmented tissue in the cavity 37 which might otherwise occlude and interfere with the rotation of the spindle 62 is flushed away therefrom. The leakage or effluent also functions as a liquid bearing between a shoulder 93 of the hub 39 which abuts the upper surface 64 of the housing 53 and further assists in flushing the fragmented tissue through the tubing 36 to the collector 15.

The pressurized fluid 9 also flows through the bores 80, 81 and 85. The fluid jets 87 radiating outwardly from the orifices 73 of the nozzle 72 impinge on the selected tissue area 3. As the spindle 62 with the attached nozzle 72 spins, the point of impingement of each jet 87 with the tissue surface 3 describes a generally circular pattern. By selectively manually maneuvering the hand-held portion 6 of the apparatus 1, the surgeon can cause the impinging jets 87 to be directed over the entire diseased area 4 including the healthy tissue 5 contiguous thereto. The impact force of each of the jets 87 is adjusted such that, when the jets 87 come in contact with the body tissue 3, only the diseased tissue 4 will be fragmented and flushed away. The healthy tissue 5 will remain intact.

The entire hand-held portion 6 of the apparatus 1 can be manually maneuvered toward or away from the operative tissue area 3 such that a gap 93 between the distal end of the shield 49 and the surface of the operative tissue area 3 is variable. By manually varying the position of the apparatus hand-held portion 6 relative to the surface of the operative area 3, the volume of ambient air admitted into the partial vacuum of the cavity 52 is accordingly controlled such that the aspiration of expended fluid and fragmented body tissue from the operative tissue area 3 is increased or decreased by the surgeon as needed.

The shield 49 serves the further purpose of minimizing the amount of fluid which would otherwise spray to surrounding areas after the jets 87 impact with the operative tissue 3. Intermediate between the extension 34 and the vacuum pump 13 is the collector 15 which collects the fluid and fragmented body tissue that is aspirated from the operative area. A vacuum control valve 94 or other control device may be inserted between the vacuum pump 13 and the collector 15 to provide control over the suction conveyed to the lance cavities 37, 38, 51 and 52. Subsequent to impingement of the jets 87 with the tissue 3, the fluid which has already expended its kinetic energy upon the tissue 3, and the tissue fragmented thereby, are aspirated away.

As the success or failure of many tumor or cancer surgeries rely on the completeness of the removal of all finger-like extensions 95 radiating outward from the core of the diseased tissue 4, the use of this apparatus 1 is very effective in that the force from the jets 87 at the points of impact of the jets 87 with the tissue area 3 is such that fragmentation can trace the finger-like extensions 95 and channel out the diseased tissue, leaving the healthy tissue 5 around such finger-like extensions 95 intact. In addition, hemostatic and other medicated agents may be added to the fluid 9 upstream from the jets 87 to reduce bleeding and enhance the healing process. The apparatus is designed such that internal parts can be easily and quickly disassembled for cleaning and sterilization purposes.

Another advantage of the current invention is that the angle with which the jets 87 radiates from the nozzle 72 permits the fragmentation of unhealthy tissue, such as the extension 95, under healthy skin tissue, thereby expediting the healing process by avoiding the unnecessary removal of healthy skin tissue as experienced with other surgical techniques. The apparatus hand-held portion 6 is sized and balanced to facilitate one-handed operation, leaving the surgeon's other hand free for other surgical necessities.

It is foreseen that motor means (such as an electric motor) other than the action of the fluid on the vanes may be utilized to rotate the spindle and nozzle.

The reference numeral 101 generally designates a modified liquid lance apparatus according to the present invention, as illustrated in FIGS. 7, 8 and 9. The apparatus 101 is used for applications where it is desirable to use a non-rotating fluid jet, especially where the jet is to be directed on a particular small operative spot as determined by a surgeon. The lance 101 is particularly adapted to facilitate disassembly thereof. Many of the features of this modified embodiment are similar in nature to those previously described for the apparatus 1 and will not be reiterated in detail here.

The modified apparatus 101 comprises a body 103 which has an elongated, narrow, cylindrically-shaped or tubular shell configuration. The body 103 has an upper end 105 and a lower end 107. A hollow tube 110 is spaced axially within the body 103 such that an upper end 112 protrudes beyond the upper body end 105 to function as a fluid input port 114. The end 112 is partially threaded to mate with threads of a knurled retaining nut 116. The tube 110 is dimensioned and constructed of suitable material to reliably withstand a fluid pressure in the operative range of the modified apparatus 101.

A lower end 118 of the tube 110 is secured to an orifice and needle-type valve 119 with a fluid seal therebetween. An O-ring washer 120 between the tube lower end 118 or hub of the valve 119 forms a liquid and vacuum seal between the hub or tube end 118 and the walls of an axial bore 122 through the lower end 107 of the body 103.

Extending radially outward from the valve 119 is a radial portion 124 which is attached to a cylindrically-shaped knurled knob 126. The radial portion 124 is constructed such that substantial axially extending voids or open passageways 128 exist therein to permit aspiration of fluids and fragmented tissue therethrough as hereinafter described, with sufficient connective and bridging spokes, such as those shown at 130 in FIG. 8, between the passageways 128 in the radial portion 124 to permit reliable opening and closing adjustment of the valve 119 by turning the knurled knob 126 clockwise or counterclockwise as required. Positioned radially outward from the passageways 128 and between the radial portion 124 and the distal end 107 of the body 103 is an O-ring or other suitable washer 132 to provide a slidable vacuum and liquid seal therebetween. A groove 134 is machined or otherwise formed in a lower planar face 136 of the end 107 or in an upper planar face 138 of the radial portion 124 of the pressure adjuster 119, or in both the lower planar face 136 and the upper planar face 138, to receive the O-ring washer 132 therein.

Similarly, an O-ring washer 142 forms a liquid and vacuum seal between the tube 110 and the walls of an axial bore 144 through the upper end 105 of the body 103.

In an assembled configuration, the nut 116 is tightened against an upper planar face 146 of the upper body end 105 such that the O-ring washer 132 is compressed between faces 136 and 138, forming a liquid and vacuum seal therebetween.

A hollow sleeve 148 is secured to the distal end of the valve 119. Frictionally, threadedly or otherwise secured to the protruding end of the sleeve 148 is an adaptor 150. As with the knurled knob radial portion 124, the adaptor 150 also has a radial portion 152 which consists largely of voids or open passageways 154. Positioned between a lower planar face 156 of the pressure adjuster radial portion 124 and an upper planar face 158 of the adaptor radial portion 152 is an O-ring washer 160 that is spaced radially outward from the passageways 128 and 154. By tightening the adaptor 150, the O-ring washer 160 is compressed between faces 156 and 158 to form a slidable vacuum and liquid seal therebetween.

Frictionally, threadedly or otherwise secured to a flange 162 near the outer perimeter of the adaptor 150 is a shield 164 which is constructed of poly(methyl methacrylate)-type polymers marketed under the trademark Plexiglas or other clear transparent material. The shield 164 is generally bell, cylindrically or spherically-shaped. The shield 164 has a lower edge 166 and contains a cavity 168.

Threadedly, by set-screw, or otherwise secured to the protruding end 170 of the sleeve 148 is a nozzle 172. The tube 110, the valve 119, the sleeve 148 and the nozzle 172 in unison communicate the input port 114 with the shield cavity 168.

At the upper end 105 of the body 103 is a vacuum output port 174 which communicates with a cavity 176 contained within body 103. Passageways 178 in the lower body end 107, the knurled knob radial portion passageways 128, and the adaptor radial portion passageways 154 communicate the body cavity 176 with the shield cavity 168.

During use of the modified apparatus 101, pressurized fluid is supplied by mechanism 180, such as the reservoir and pump in the previous embodiment, to the input port 114 and an aspirating and specimen collecting mechanism 182, such as the vacuum pump and collector of the previous embodiment, is attached to the output port 174. A surgeon grasps the elongated body 103 in his hand and positions the edge 166 of the shield 164 over and slightly above the tissue 184 to be fragmented.

With a free hand, the surgeon then manipulates the knurled knob 126 to adjust the force with which a liquid jet 186 emerging from the nozzle 172 impacts with the operative tissue surface 184. Because of the readily accessible location of the knurled knob 126, the surgeon may readjust the impact force from time to time as needed during the operative process.

As the jet 186 impacts with the tissue surface 184, the shield 164 essentially restrains the expended fluid and fragmented tissue from spraying to regions beyond the operative tissue area. By arbitrarily maneuvering the outer edge 166 of the shield 164 toward or away from the operative tissue surface 184, the surgeon can dynamically control air flow into the cavity 168 and thereby control the rate of aspiration of the effluent and fragmented tissue from the operative site. The effluent and fragmented tissue is aspirated through the openings 154, 128 and 178 and through the output port 174 into a specimen collector (not shown).

By viewing the operative area through the transparent shield 164, the surgeon can effectively maneuver the impact point of the jet 186 relative to the operative tissue surface 184 until the diseased tissue 188 has been fragmented and removed therefrom.

To facilitate cleaning the various internal parts of the hand-held portion 101 of the apparatus, the retaining nut 116 can be removed and the hand-held portion 101 dismantled by withdrawing the tube 110, the pressure adjuster 124 and parts attached thereto from the distal end 107 of the body 103. The nozzle 172 and the adaptor 150 can also be removed to provide further disassembly for cleaning, maintenance and part replacement purposes.

The method of using each apparatus 1 and 101 to remove diseased or cancerous tissue functions well for a wide range of cancer and other diseases where the disease causes a change in the structure of the tissue (or bone) so that the structure is weakened and can thus be removed at a discrete jet pressure, sufficient to remove the diseased tissue, while still not having enough force to damage surrounding healthy tissue.

It is to be understood that while certain forms of the present invention have been illustrated and described herein, it is not to be limited to the specific forms or arrangement of parts described and shown.

What is claimed and desired to be secured by Letters Patent is as follows:

1. A surgical apparatus for removing diseased tissue from non-diseased animal or human tissue comprising:
   (a) liquid jet producing means operably movable by a surgeon over tissue to be removed;
   (b) fluid pressurization means for pressurizing fluid and delivering the fluid under pressure to said liquid jet producing means;
   (c) said liquid jet producing means for operably producing a narrow jet of pressurized fluid to be directed toward the tissue to be removed by the surgeon;
   (d) said jet producing means being adapted for removing tumors from skin wherein said tumors have fingers that extend under healthy skin tissue; and including:
   (e) angled nozzle means secured to a liquid jet exiting end of said jet producing means directing said jet of pressurized fluid at an angle other than perpendicular to skin tissue so as to allow for removal of the tumor fingers by the jet; and
   (f) rotating means positioned within said apparatus for cooperating with and rotating said nozzle means such that a point of impact of said jet describes a generally circular pattern relative to the tissue during use.

2. The apparatus according to claim 1 including:
   (a) means for adjusting the pressure of said fluid such that the impact of said jet selectively fragments said diseased tissue while leaving juxtaposed healthy tissue intact.

3. The surgical apparatus according to claim 1 including:
   (a) suctioning means secured to said liquid jet producing means and operating to aspirate effluent and fragmented tissue from the operative site.

4. A surgical apparatus comprising:
   (a) a liquid jet lance;
   (b) said lance including a hand-held body and a spindle having an axis of rotation with an attached nozzle having an orifice for emitting a jet of fluid at an oblique angle relative to said spindle axis;
   (c) said spindle being rotatable relative to said body and including rotating means;
   (d) fluid pressurizing means flow connected to said lance; and
   (e) vacuum aspirating and specimen collecting means flow connected to said lance whereby said jet may be selectively utilized by a surgeon to remove diseased tissue from surrounding healthy tissue.

5. The apparatus according to claim 6 including:
   (a) a shield projecting from said body so as to be positioned between a surgeon using the apparatus and the diseased tissue to be removed during use of said apparatus.

6. The apparatus according to claim 5 wherein:
   (a) said shield is constructed of a clear material to allow a surgeon to view the diseased tissue during use of the apparatus.

7. The apparatus according to claim 4 wherein:
   (a) said orifice is aligned such that the liquid jet is emitted at an angle of approximately 15° relative to said spindle axis of rotation.

8. A surgical apparatus for removing tumors and related diseased tissue from skin comprising:
   (a) a hand-held lance including a body, a housing positioned within said body, a spindle rotatable within said housing and nozzle means;
   (b) said housing being slidably positioned by O-ring-type washers within said body such that the displacement of said housing relative to said lance body can be adjusted to locate said nozzle farther from or closer to said operative surface;
   (c) said spindle being rotated about an axis of rotation within said housing by pressurized fluid impacting with vanes contoured on the surface of said spindle; rotation of said spindle being facilitated by the semi-tangential impingement of pressurized fluid on said vanes;
   (d) said nozzle means connected to and rotating with said spindle; said nozzle means being adapted to emit a narrow jet of said pressurized fluid at an oblique angle to said spindle axis of rotation such that rotation of said nozzle means causes the points of impact of said jet on the tissue to describe a generally circular pattern at the operative site; said nozzle means adapted to provide a jet with sufficient energy at impact and at a substantial angle relative to perpendicular to the tissue to effectively fragment diseased tissue in finger-like extensions while leaving overlying healthy tissue intact; said nozzle means adapted to produce a liquid jet having a relatively small cross-sectional area; said nozzle means being operably positioned relative to said lance body by a keeper ring;
   (e) pressurized fluid means flow connected to said lance for providing pressurized fluid to said lance;
   (f) channel means within said lance to distribute pressurized fluid therethrough; said channel means flow connected to said pressurized fluid means so as to be adapted to receive fluid under pressure therefrom; said channel means adapted to distribute fluid under pressure to said vanes and to said nozzle means;
   (g) a first of said spindle and said housing having circumferential grooves positioned therealong so as to face a second of said spindle and said housing; said channel means adapted to distribute pressurized fluid to said grooves during operation of said lance so as to form a liquid bearing between said spindle and said housing;
   (h) a transparent shield attached to the distal end of said hand-held lance; said shield positioned so as to reduce the spray of fluid and fragmented tissue onto the operator during use; said shield providing relatively unobscured visibility of the tissue to the operator;

(i) aspiration means for aspiration of fragmented tissue along with fluid after the fluid has impinged on the tissue; said aspiration means flow connected to said lance; said lance including a passageway therethrough and a lower cavity encircled by said shield flow connected to said aspiration means so as to draw used fluid and fragmented tissue through said passageway to said aspiration means during use;

(j) collecting means imposed between said aspiration means and said lance to collect specimens of the fragmented tissue; and (k) said hand-held lance being selectively manipulatable such that said shield is variably spacable from the tissue so as to produce a variable air gap to adjust air flow into said aspiration means.

9. The apparatus according to claim 8 wherein:
(a) said orifice diameter is between 0.001 and 0.030 inches.

10. The apparatus according to claim 8 wherein:
(a) said orifice diameter is 0.015 inches.

11. The apparatus according to claim 8 wherein:
(a) said nozzle includes multiple orifices; each of said multiple orifices adapted to produce a liquid jet in different directions relative to one another.

12. The apparatus according to claim 8 including pressure adjustment means for selectively varying the pressure of liquid at the lance nozzle means.

13. A surgical liquid jet apparatus comprising:
(a) a hand-held lance with a source of pressurized fluid;
(b) said lance including nozzle means secured to a liquid jet exiting end of said lance; said nozzle means adapted to emit said fluid from said lance in the form of a relatively narrow liquid jet with sufficient impact energy to fragment diseased and cancerous tissue without removing healthy tissue;
(c) pressure adjustment means adapted to vary the pressure of the liquid delivered to said lance;
(d) viewing means including a clear shield secured to said lance so as to be adapted to be positioned between said nozzle means and a user of said apparatus for allowing a user to observe an operative area during use of said lance, while preventing a user from being sprayed by fluid that is sprayed against said shield; and
(e) aspiration means secured to said lance and adapted to remove liquid effluent and fragmented tissue during use of said lance.

14. The apparatus according to claim 13 including:
(a) seal means within said lance to prevent leakage of pressurized fluid and to maintain vacuum of said aspiration means therein.

15. The apparatus according to claim 13 wherein:
(a) said lance includes a housing and a spindle rotatable within said housing; said nozzle means being attached to said spindle; and
(b) said spindle being removably mounted within said housing to allow for cleaning of said spindle.

16. A surgical method for removing diseased tissue from otherwise healthy skin tissue comprising the steps of:
(a) directing a relatively thin jet of fluid to impact against said diseased tissue to fragment the diseased tissue, but insufficient to destroy healthy surrounding tissue;
(b) mechanically moving a point of impact of said jet so as to impact the tissue in a generally circular pattern.

17. The method according to claim 16 wherein:
(a) said jet is directed toward said tissue at a substantial angle relative to perpendicular so as to impinge upon and remove extensions of diseased tissue beneath healthy tissue.

18. The method according to claim 16 including the step of:
(a) aspirating and collecting fluid subsequent to said fluid impinging on the tissue along with fragments of the diseased tissue dislodged from the healthy tissue.

19. A surgical apparatus for removing diseased tissue from non-diseased animal or human tissue comprising:
(a) a liquid jet producing means operably movable by a surgeon over tissue to be removed;
(b) fluid pressurization means for pressurizing fluid and delivering the fluid under pressure to said liquid jet producing means;
(c) said liquid jet producing means for operably producing a narrow jet of pressurized fluid to be directed toward the tissue to be removed by the surgeon;
(d) suctioning means secured to said liquid jet producing means and operating to aspirate effluent and fragmented tissue from the operative site;
(e) said jet producing means being adapted for removing tumors from skin wherein said tumors have fingers that extend under healthy skin tissue; and including:
(f) angled nozzle means secured to a liquid jet exiting end of said jet producing means directing said jet of pressurized fluid at an angle other than perpendicular to skin tissue so as to allow for removal of the tumor fingers by the jet; and
(g) rotating means positioned within said apparatus for cooperating with and rotating said nozzle means such that a point of impact of said jet describes a generally circular pattern relative to the tissue during use.

20. A surgical liquid jet apparatus comprising:
(a) a hand-held lance with a source of pressurized fluid;
(b) said lance including nozzle means secured to a liquid jet exiting end of said lance; said nozzle means adapted to emit said fluid from said lance in the form of a relatively narrow liquid jet with sufficient impact energy to fragment diseased and cancerous tissue without removing healthy tissue;
(c) pressure adjustment means adapated to vary the pressure of the liquid delivered to said lance;
(d) viewing means secured to said lance so as to be adapted to be positioned between said nozzle means and a user of said apparatus for observing an operative area during use of said lance;
(e) aspiration means secured to said lance and adapted to remove liquid effluent and fragmented tissue during use of said lance;
(f) said lance includes a housing and a spindle rotatable within said housing; said nozzle means being attached to said spindle; and
(g) said spindle being removably mounted within said housing to allow for cleaning of said spindle.

* * * * *